United States Patent [19]
Kusakabe et al.

[11] 3,930,955
[45] Jan. 6, 1976

[54] PROCESS FOR PRODUCING PTERIN DEAMINASES HAVING ANTITUMOR ACTIVITY

[75] Inventors: Hitoshi Kusakabe; Kenjiro Kodama; Yuichirow Midorikawa; Haruhiko Machida; Akira Kuninaka; Hiroshi Yoshino, all of Choshi, Japan

[73] Assignee: Yamasa Shoyu Kabushiki Kaisha, Choshi, Japan

[22] Filed: May 13, 1974

[21] Appl. No.: 469,689

[30] Foreign Application Priority Data
May 12, 1973 Japan............................ 48-52101

[52] U.S. Cl.................. 195/66 R; 195/62; 424/94
[51] Int. Cl.$^2$.................. A61K 37/48; C12D 13/10
[58] Field of Search...................... 195/62, 65, 66 R

[56] References Cited
OTHER PUBLICATIONS
Hayaishi in Methods in Enzymology, Vol. 6, pp. 359–363, (1963).

Primary Examiner—Lionel M. Shapiro
Attorney, Agent, or Firm—Wenderoth, Lind & Ponack

[57] ABSTRACT

The enzyme pterin deaminase may be used as an antitumor agent, and can be produced from cultures of the fungal genera *Aspergillus*, *Mucor*, *Rhizopus*, and *Penicillium*.

11 Claims, No Drawings

PROCESS FOR PRODUCING PTERIN DEAMINASES HAVING ANTITUMOR ACTIVITY

This invention relates to pterin deaminases having antitumor activity and to a process for producing the same by growing molds.

We have discovered that pterin deaminases, which catalyze the hydrolytic deamination of pterin, pteroic acid and folic acid yielding the corresponding 2,4-dihydroxy compounds (lumazines), as illustrated by the following generalized reaction, have antitumor activity and that the enzymes are distributed rather widely among molds, especially among the genera Aspergillus, Mucor, Rhizopus, and Penicillium.

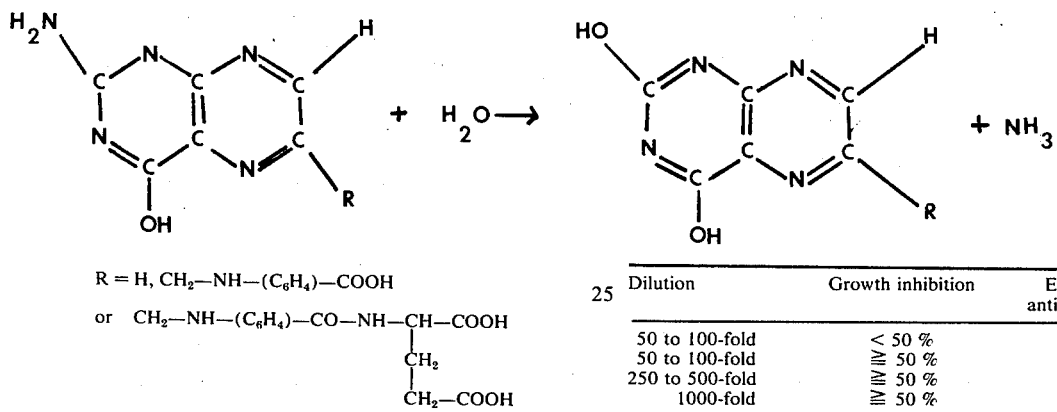

R = H, $CH_2-NH-(C_6H_4)-COOH$ or $CH_2-NH-(C_6H_4)-CO-NH-CH-COOH$
$\qquad\qquad\qquad\qquad\qquad\quad |$
$\qquad\qquad\qquad\qquad\qquad\ CH_2$
$\qquad\qquad\qquad\qquad\qquad\quad |$
$\qquad\qquad\qquad\qquad\qquad\ CH_2-COOH$ Occurrence of pterin deaminase has been reported only in rat liver (see, for example, the paper by H. Rembold et al. B. B. A. 1969, Vol. 184, No. 3, p. 589 to 596) and Alcaligenes bacteria (see the paper by McNutt A. B. B. 1963, Vol. 101, No. 1, p. 1 to 6 and the paper by Levenberg et al. J. B. C. 1959, Vol. 234, No. 4, p. 955 to 961). The Alcaligenes enzyme is produced in the cells but is not found in the medium during growth. Thus, its industrial mass production seems to be difficult. Furthermore, nobody has recognized that pterin deaminase has antitumor acitivity.

In a search for new antitumor chemotherapeutic agents, we have found that a number of microorganisms—both type cultures and newly isolated strains—belonging to the genera Aspergillus, Mucor, Rhizopus, and Penicillium contain a water-soluble substance that inhibits growth of L5178Y leukemia cells in vitro. The substance has been proved to be pterin deaminase. The enzyme can be easily extracted from the cells, especially from their solid cultures.

Typical type cultures having pterin deaminase activity are as follows:

| | |
|---|---|
| *Aspergillus tamarii* | IFO 4287 |
| *Aspergillus oryzae* | var. No. 13 |
| *Aspergillus gymnosardae* | IAM 2149 |
| *Mucor albo-ater* | IAM 6141 |
| *Mucor lamprospolus* | IAM 6114 (ATCC 20410) |
| *Rhizopus japonicus* | IAM 6002 (ATCC 20409) |
| *Rhizopus arrhizus* | IAM 6052 |

Among them *Mucor lamprospolus* IAM 6114 (ATCC 20410) and *Rhizopus japonicus* IAM 6002 (ATCC 20409) are especially rich in pterin deaminase activity.

We also have obtained a number of pterin deaminase-rich molds from soils of various Japanese districts. Representative strains are as follows:

| | |
|---|---|
| *Aspergillus* | Y 8-5 (ATCC 20413) |
| *Aspergillus* | Y 43-4 (ATCC 20414) |
| *Penicillium* | Y 70-2 (ATCC 20411) |
| *Pencicillim* | Y110-2 (ATCC 20412) |

Pterin deaminase activities and in vitro antitumor activities of the above cultures are given in Table 1.

Each strain was grown on wheat bran at 28°C for 4 days. The culture was extracted with 5 volumes of water. The extract was clarified, and pterin deaminase activity and antitumor activity (in vitro) in the extract were determined. For the sake of convenience 1 unit of pterin deaminase was defined as the amount capable of deaminating 1 m$\mu$mole of folic acid in a 0.1 M TRIS-hydrochloric acid buffer, pH 7, at 37°C for 1 minute.

For determination of in vitro antitumor activity, 0.9 ml of L5178Y cell suspension ($7 \times 10^4$ cells/ml) and 0.1 ml of sample (diluted extract of culture) were mixed. The mixture was incubated as usual at 37°C for 48 hours. Antitumor activity was expressed as follows:

| Dilution | Growth inhibition | Expression of antitumor activity |
|---|---|---|
| 50 to 100-fold | < 50 % | − |
| 50 to 100-fold | ≧ 50 % | + |
| 250 to 500-fold | ≧ 50 % | + + |
| 1000-fold | ≧ 50 % | + + + |

Table 1

Examples of pterin deaminase activities and in vitro antitumor activities in extracts of cultures of molds

| Strain | Pterin Deaminas unit/ml | Antitumor activity (in vitro L5178Y) |
|---|---|---|
| *Aspergillus tamarii* IFO4287 | 11.6 | + |
| *Aspergillus gymnosardae* IAM2149 | 24.5 | + + |
| *Mucor albo-ater* IAM6141 | 27.8 | + + |
| *Mucor lamprospolus* IAM6114 (ATCC20410) | 37.1 | + + |
| *Rhizopul japonicus* IAM6002 (ATCC20409) | 123.4 | + + + |
| *Rhizopus arrhizus* IAM6052 | 25.0 | + + |
| *Aspergillus orgyzae* var No.13 | 26.0 | + + |
| *Aspergillus* Y8-5(ATTCC20413) | 32.6 | + + |
| *Aspergillus* Y43-4(ATCC20414) | 18.8 | + + |
| *Penicillium* Y70-2(ATCC20411) | 107.0 | + + + |
| *Penicillium* Y110-2(ATCC20412) | 19.5 | + + |

Pterin deaminases obtained from the genera Aspergillus, Mucor, Rhizopus, and Penicillium commonly catalyze the hydrolytic deamination of pterin, pteroic acid and folic acid, but do not catalyze the deamination of methotrexate, dihydrofolic acid, tetrahydrofolic acid, aminopterin and folinic acid. As mentioned above, they also commonly have antitumor activity.

According to the invention, pterin deaminase having antitumor activity is readily isolated by growing a mold strain selected from the genera Aspergillus, Mucor, Rhizopus, and Penicillium upon a suitable nutrient medium until a desired quantity is obtained and then extracting the enzyme.

In processes in accordance with the present invention, pterin deaminases are obtained from microorganisms of the genera Aspergillus, Mucor, Rhizopus and Penicillium grown under any of the conditions under which growth of molds will normally take place. These microorganisms are grown in a variety of solid or liquid culture media. Although various nitrogen and carbon sources may be used, wheat bran is particularly effective for production of pterin deaminase. When the microorganisms are grown in liquid media, either the batch or continuous methods of cultivation may be used. Cultures are maintained at between 10° and 40°C, preferably 25° to 35°C, and at a pH of between about 5 and 9.

Pterin deaminase according to the present invention has been proved to have a particular antitumor activity: The enzyme inhibits growth of L5178Y leukemia cells in vitro. The enzyme also significantly increases the average life-span of the mice injected intraperitoneally with L1210 leukemia cells and inhibits growth of B16 melanoma cells injected subcutaneously into mice. The antitumor activity can be recognized even in a crude preparation, such as the extract of the mold culture on wheat bran (in vitro test) or its partially purified preparation (in vivo test).

For example, the extract of culture of Aspergillus Y8-5 has in vitro antitumor activity as follows:

Aspergillus Y8-5 (ATCC 20413) was grown on wheat bran at 28°C for 4 days. The culture was extracted with 5 volumes of water. The clarified extract contained 32.0 unit/ml of pterin deaminase whose specific activity was 8.0 unit/mg protein. The extract inhibited growth of murine L5178Y leukemia cells under the following conditions: L5178Y cells were grown at 37°C in a tube containing 5 ml of RPMI 1640 medium containing 10 % calf serum for 96 hr. To the cell suspension, 1/9 volume of the 1000-fold, 500-fold, or 125-fold diluted extract was added. As shown in Table 2, 50 % to 70 % inhibitions of the growth of L5178Y cells were recognized after addition of the 1000-fold and 125-fold (or 500-fold) diluted extracts, respectively.

Table 2

Growth of L5178Y cells in the presence or absence of the extract of Aspergillus Y8-5 grown on wheat bran

| Tube No. | Days after addition | Number of cells ×10⁴/ml. | % of control |
|---|---|---|---|
| 1 | 0 | 7.0 | — |
| 1 | 2 | 80 | 100 |
| 2 | 2 | 54 | 67.5 |
| 3 | 2 | 30 | 37.5 |
| 4 | 2 | 27 | 33.8 |
| 1 | 3 | 181 | 100 |
| 2 | 3 | 92 | 50.8 |
| 3 | 3 | 61 | 33.7 |
| 4 | 3 | 60 | 33.1 |
| 1 | 4 | 200 | 100 |
| 2 | 4 | 101 | 50.5 |
| 3 | 4 | 78 | 39.0 |
| 4 | 4 | 71 | 35.5 |

Tube 1: No addition,
Tube 2: Addition of the 1000-fold diluted extract,
Tube 3: Addition of 500-fold diluted extract,
Tube 4: Addition of 125-fold diluted extract.

It was concluded that the inhibitory agent in the extract was pterin deaminase. The conclusion is supported by the following experiments:
1. L5178Y cells could not normally grow in a medium that had been incubated previously with the acetone-precipitated fraction of the extract then heated at 65°C for 30 minutes to inactivate the agent. The longer preincubation with the more concentrated agent resulted in poorer growth of L5178Y cells. During the preincubation, folate in the medium was confirmed to be deaminated to its lumazine type with formation of ammonia.
2. The growth of L5178Y cells in the preincubated medium was completely reversed by adding folate, but not by the other vitamins.

Extracts of cultures of molds other than Aspergillus Y8-5 have the similar in vitro antitumor activity. In addition, in vivo antitumor activity of pterin deaminase will be illustrated in the Examples.

Lately, a carboxypeptidase that produces pteroate by removing the terminal glutamate residue of the folate molecule was recognized to have antitumor activity. (See the paper by B. A. Chabner et al., Cancer Research 1972, Vol. 32, No. 10, p. 2114 to 2119). For folate-depletion therapy in malignant and other diseases, however, pterin deaminase seems to be more effective than the carboxypeptidase because the former completely inactivates folic acid by transforming pterin structure into biologically inactive lumazine structure, while the latter does not catalyze any reaction related to the transformation of pterin moiety of folic acid.

The present invention also provides pharmaceutical compositions comprising pterin deaminase according to the present invention in combination with a pharmaceutically-acceptable carrier or diluent therefor.

The present invention will now be illustrated by the following Examples.

EXAMPLE 1

Aspergillus Y8-5 (ATCC 20413) was grown on 40 kg of wheat bran at 28°C for 4 days. The culture was extracted with 200 l of water. To the extract (190 l) containing about 2 million units of pterin deaminase, 1.7 volumes of acetone were added to precipitate the enzyme. The enzyme was extracted with 7.0 l of 0.02 M Tris-HCl buffer, pH 7.0, from the precipitate, dialyzed against 0.02 M Tris-HCl buffer, pH 7.0, for 24 hours, and decolored with 3 % active carbon. A part of the carbon-treated preparation containing 960,000 units of the enzyme was purified with DEAE-cellulose column chromatography, sephadex G-75 gel filtration, concentration, and removal of insoluble impurities with centrifugation. The partially purified preparation was lyophilyzed. The lyophilyzed preparation, whose protein content was 76.1 %, is referred to as "Preparation I." Preparation I (1.629 g) contained 268,785 units of pterin deaminase. Thus, the enzyme activity is calculated to be 165 units/mg of powder (235 units/mg of protein).

The antitumor activity of Preparation I was tested, and the results as set forth in Table 3 were obtained.

Table 3

| Sample tested | Dose units/mouse /day | Mean survival days (T/C)* | Increase in life span over controls (%) |
|---|---|---|---|
| Preparation I | 200 | 8.4/7.0 | 20.0 |
| | 60 | 7.5/7.0 | 7.2 |
| | 6 | 7.3/7.0 | 4.2 |

In the test, mice were inoculated intraperitoneally with $1 \times 10^5$ cells of L-1210 leukemia. The sample was injected intraperitoneally once daily for 5 consecutive days starting 24 hr after transplantation. Antitumor activity was evaluated by the increase in life span over controls (%). *T/C= treated group/control group.

EXAMPLE 2

A part of Preparation I (0.75g) was further purified by DEAE-cellulose column chromatography. The resulting lyophilyzed powder, Preparation II (103mg), contained 84,975 units of pterin deaminase. The enzyme activity is calculated to be 825 units/mg of powder (1428 units/mg of protein).

The antitumor activity of Preparation II was tested, and the results set forth in Table 4 were obtained.

Table 4

| Sample tested | Dose units/mouse/day | Inhibition of tumor growth (%) |
|---|---|---|
| Preparation II | 400 × 5 | 38 |
|  | 200 × 5 | 45 |
|  | 100 × 5 | 22 |
| Control (PBS) | — | 0 |

In the test, male C57BL mice weighing 20 ± 2g were used, and $10^6$ cells of melanoma B16 were implanted subcutaneously. Administration of samples was made subcutaneously for 5 consecutive days starting 24 hr after tumor transplantation. A control group was administered with 0.2 ml of Dulbecco's phosphate buffered saline (PBS), which was a solvent solution for Preparation II.

EXAMPLE 3

Penicillium Y70-2 (ATCC 20414) was grown on 4 kg of wheat bran at 28°C for 4 days. The culture was extracted with water, and pterin deaminase was purified from the extract in the essentially same way as specified in Example 2. The powder thus obtained, Preparation III (210mg), contained 323,000 units of pterin deaminase. The enzyme activity is calculated to be 1,430 units/mg of powder (1,790 units/mg of protein).

The antitumor activity of Preparation III was tested, and the results thus obtained are set forth in Table 5.

Table 5

| Sample treated | Dose units/mouse/day | Inhibition of tumor growth (%) |
|---|---|---|
| Preparation III | 400 × 9 | 51 |
|  | 200 × 9 | 57 |
|  | 100 × 9 | 34 |
| Control (PBS) | — | 0 |

In the test, samples were injected subcutaneously for 9 consecutive days from 24 hr after transplantation of $10^6$ cells of melanoma B16.

We claim:
1. A process for the production of pterin deaminase which comprises growing a microorganism selected from the genera Aspergillus, Mucor, Rhizopus, and Penicillium, extracting pterin deaminase, and isolating the extracted pterin deaminase.
2. A process according to claim 1 wherein the microorganism is of the species *Aspergillus oryzae*.
3. A process according to claim 1 wherein the microorganism is of the species *Aspergillus tamarii*.
4. A process according to claim 1 wherein the microorganism is of the species *Rhizopus japonicus*.
5. A process according to claim 1 wherein the microorganism is of the species *Mucor lamprosporus*.
6. A process according to claim 1 wherein the microorganism is Penicillium Y70-2, ATCC 20411.
7. A process according to claim 1 wherein the microorganism is Aspergillus Y8-5, ATCC 20413.
8. A process according to claim 1 in which the culture medium is a solid culture medium.
9. A process according to claim 1 in which the culture medium contains wheat bran.
10. A process according to claim 1 in which the temperature is maintained between about 10° and 40°C.
11. A process according to claim 1 in which the pH is maintained between about 5 and 9.

* * * * *